(12) United States Patent
Nishioka et al.

(10) Patent No.: US 8,222,276 B2
(45) Date of Patent: *Jul. 17, 2012

(54) AMINE SALT OF CARBOSTYRIL DERIVATIVE

(75) Inventors: Yoshihiro Nishioka, Tokushima (JP); Shinji Aki, Tokushima (JP); Shigekazu Fujita, Okazaki (JP); Yoshinao Onishi, Tokushima (JP); Shun-ichiro Sumida, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 169 days.

This patent is subject to a terminal disclaimer.

(21) Appl. No.: 12/662,610

(22) Filed: Apr. 26, 2010

(65) Prior Publication Data

US 2010/0210684 A1 Aug. 19, 2010

Related U.S. Application Data

(63) Continuation of application No. 10/586,453, filed as application No. PCT/JP2005/001034 on Jan. 20, 2005, now Pat. No. 7,732,611.

(30) Foreign Application Priority Data

Jan. 21, 2004 (JP) ................................. 2004-013402

(51) Int. Cl.
*A61K 31/04* (2006.01)
*C07D 215/38* (2006.01)

(52) U.S. Cl. ...................................... 514/312; 546/159
(58) Field of Classification Search .................. 546/159; 514/312

See application file for complete search history.

(56) References Cited

U.S. PATENT DOCUMENTS

| | | | |
|---|---|---|---|
| 4,578,381 A | 3/1986 | Uchida et al. | |
| RE34,722 E | 9/1994 | Uchida | |
| 5,415,872 A | 5/1995 | Sipos | |
| 5,476,858 A | 12/1995 | Yamasaki et al. | |
| 5,480,891 A | 1/1996 | Yamasaki et al. | |
| 5,576,331 A | 11/1996 | Yamasaki et al. | |
| 5,637,597 A | 6/1997 | Matsuda et al. | |
| 6,060,486 A | 5/2000 | Urashima et al. | |
| 7,732,611 B2 * | 6/2010 | Nishioka et al. | 546/159 |

FOREIGN PATENT DOCUMENTS

| | | |
|---|---|---|
| JP | 47-19917 | 6/1972 |
| JP | 8-295673 | 11/1996 |
| JP | 2000-512988 | 10/2000 |
| JP | 2005-519949 | 7/2005 |
| KR | 1020040104020 A | 12/2004 |
| WO | WO 95/12579 | 5/1995 |
| WO | WO 97/13515 | 4/1997 |
| WO | WO 97/49693 | 12/1997 |
| WO | WO 03/076393 A1 | 9/2003 |

OTHER PUBLICATIONS

Nathan L. Drake et al., "Synthetic Antimalarials, The Preparation of Certain 4-Aminoquinolines[1]," *J. Am. Chem. Soc.*, 1946, 68 (7), pp. 1208-1213.

Robert C. Elderfield et al., "Synthesis of Potential Anticancer Agents. III. Nitrogen Mustards Derived from 8-Aminoquinolines[1-3]," *J. Org. Chem.*, 1960, 25(9), pp. 1576-1583.

Office Action dated Nov. 25, 2010 issued in corresponding Indian Application No. 4311/delnp/2006.

Abstract of M. Uchida et al., "Studies on 2(1H)-quinolinone derivatives as gastric antiulcer active agents. Synthesis and anticulcer activities of optically active .alpha.-amino acid derivatives of 2(1H)-quinolinone and oxindole," Chemical and Pharmaceutical Bulletin, vol. 35, No. 2, 1987, pp. 853-856.

C. G. Wermuth (ED), Bradley D. Anderson & Karl P. Flora, The Practice of Medical Chemistry, Sep. 25, 1999, pp. 347-365.

* cited by examiner

*Primary Examiner* — D M Seaman
(74) *Attorney, Agent, or Firm* — Finnegan, Henderson, Farabow, Garrett & Dunner, L.L.P.

(57) ABSTRACT

The invention provides an amine salt of a carbostyril derivative formed from a carbostyril derivative represented by the formula (1) [wherein R is a halogen atom; the substituted position of the side chain is 3- or 4-position in the carbostyril skeleton; and the bonding between 3- and 4-positions of the carbostyril skeleton is a single bond or a double bond] and an amine; and the invention is useful as drugs for treating various diseases, especially as aqueous formulations due to the superior water solubility and the superior pharmacologic effects.

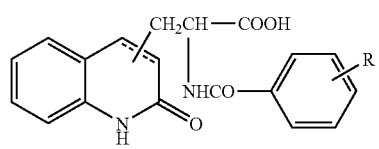

(1)

3 Claims, No Drawings

AMINE SALT OF CARBOSTYRIL DERIVATIVE

This application is a continuation of application Ser. No. 10/586,453, filed Jul. 18, 2006, now U.S. Pat. No. 7,732,611, which is a §371 of International application No. PCT/JP2005/001034 filed Jan. 20, 2005, which claims priority of Japanese application No. 2004-013402 filed Jan. 21, 2004, the contents of all of which are incorporated herein by reference.

TECHNICAL FIELD

The present invention relates to pharmaceutically useful and novel amine salts of a carbostyril derivative, more specifically, amine salts of a carbostyril derivative formed from a carbostyril derivative represented by the formula (1):

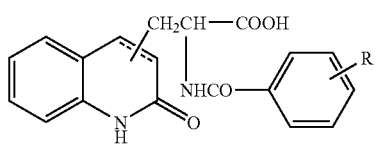
(1)

wherein:
R is a halogen atom,
the substituted position of the side chain is 3- or 4-position in the carbostyril skeleton, and
the bonding between 3- and 4-positions of the carbostyril skeleton is a single bond or a double bond, and an amine; and pharmaceutical formulations comprising the amine salt of the carbostyril derivative as the active ingredient.

BACKGROUND ART

The carbostyril derivatives represented by the general formula (1) are known to be useful as an anti-ulcer agent (JP-B-63-35623). The representative example of the derivative, 2-(4-chlorobenzoylamino)-3-(2-quinolon-4-yl)-propionic acid, is a commercially available medicine, but the formulation thereof is limited to a solid formulation for oral administration or a suspension type liquid formulation (an ophthalmic suspension, an enema, and a gargle) since the compound is very little soluble in water. Suspension type liquid formulations have several problems in the preparation, such as difficulty in keeping of uniformity of contents; necessity of controlling the particle distribution; necessity of use of a suspending agent, a dispersing agent and the like; impossibility of the terminal sterilization by steam or the sterilization by filtration; etc. On the contrary, formulations in the form of a solution have some advantages such as rapid absorption compared with solid formulations and suspension type liquid formulations, and hence it is desirable to formulate the carbostyril derivatives in the form of a solution, such as injections, ophthalmic solutions, oral solutions, enemas, gargles, ear droppers, nasal drops, and external preparations.

The carbostyril derivatives represented by the above general formula (1) and the preparation thereof are disclosed in JP-B-63-35623. It is also known that the carbostyril derivatives are formed into a bismuth salt thereof, a carboxylate-bismuth complex thereof, and a salt with a diamine derivative or a piperazine derivative (WO 95/12579 and JP-A-8-295673). However, such salts also have low solubility in water.

DISCLOSURE OF INVENTION

The present invention is to provide a novel salt of a carbostyril derivative represented by the general formula (1) which can dissolve the above problems.

The present inventors have extensively studied to find a salt of the carbostyril derivative of the formula (1) which has superior water-solubility, and have found that an amine salt of the carbostyril derivative of the above-mentioned formula (1) exhibits the desired excellent water-solubility. Based upon the new findings, the present invention has been completed.

The present invention includes a variety of embodiments as follows:

1. An amine salt of a carbostyril derivative formed from a carbostyril derivative represented by the formula (1):

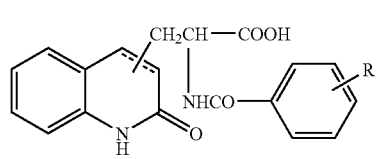
(1)

wherein R, the substituted position of the side chain, and the bonding between 3- and 4-positions of the carbostyril skeleton are as defined above,
and an amine.

2. The amine salt of the carbostyril derivative according to the above 1, wherein said carbostyril derivative (1) is 2-(4-chlorobenzoylamino)-3-(2-quinolon-4-yl)propionic acid.

3. The amine salt of the carbostyril derivative according to the above 2, wherein said amine is L-arginine.

4. The amine salt of the carbostyril derivative according to the above 2, wherein said amine is L-lysine.

5. The amine salt of the carbostyril derivative according to the above 2, wherein said amine is ethylenediamine.

6. The amine salt of the carbostyril derivative according to the above 2, wherein said amine is tris(hydroxymethyl)-aminomethane.

7. The amine salt of the carbostyril derivative according to the above 2, wherein said amine is monoethanolamine.

8. The amine salt of the carbostyril derivative according to the above 2, wherein said amine is diethanolamine.

9. The amine salt of the carbostyril derivative according to the above 2, wherein said amine is diisopropanolamine.

10. The amine salt of the carbostyril derivative according to the above 2, wherein said amine is meglumine.

11. A pharmaceutical formulation comprising the amine salt of the carbostyril derivative according to any one of the above 1-10 as the active ingredient.

12. A pharmaceutical formulation comprising a carbostyril derivative represented by the above formula (1) and an amine, which may be prepared in the form of an aqueous solution by adding an aqueous solvent when used.

13. The pharmaceutical formulation to be prepared in a preparation when used according to the above 12, wherein said carbostyril derivative (1) is 2-(4-chlorobenzoylamino)-3-(2-quinolon-4-yl)propionic acid.

14. The pharmaceutical formulation to be prepared in a preparation when used according to the above 13, wherein said amine is L-arginine.

15. The pharmaceutical formulation to be prepared in a preparation when used according to the above 13, wherein said amine is L-lysine.

16. The pharmaceutical formulation to be prepared in a preparation when used according to the above 13, wherein said amine is ethylenediamine.

17. The pharmaceutical formulation to be prepared in a preparation when used according to the above 13, wherein said amine is tris(hydroxymethyl)aminomethane.

18. The pharmaceutical formulation to be prepared in a preparation when used according to the above 13, wherein said amine is monoethanolamine.

19. The pharmaceutical formulation to be prepared in a preparation when used according to the above 13, wherein said amine is diethanolamine.

20. The pharmaceutical formulation to be prepared in a preparation when used according to the above 13, wherein said amine is diisopropanolamine.

21. The pharmaceutical formulation to be prepared in a preparation when used according to the above 13, wherein said amine is meglumine.

The halogen atom of group R in the above formula (1) means a fluorine, chlorine, bromine or iodine atom.

The amine includes an amino acid, a lower alkyl-substituted amine which may have a substituent selected from the group consisting of hydroxy group and amino group, an amino sugar, and the like. The amino acid includes a basic amino acid such as L-arginine, L-lysine, L-histidine, $\beta$-amino-alanine, $\gamma$-amino-butyrine, ornithine, $\delta$-hydroxy-lysine, canavanine, lombricine, homoarginine, $\gamma$-hydroxy-homoarginine, $\gamma$-hydroxy-L-arginine, $\beta$-alanine, $\gamma$-amino-butyric acid, $\beta$-amino-isobutyric acid, $\gamma$-amino-$\beta$-methylenebutyric acid, creatine, rhodoic acid, sarcosine, $\gamma$-amino-$\alpha$-methylenebutyric acid, kynurenine, agritine, L-tryptophan, ibotenic acid, lathyrine, tricholomic acid, quisqualic acid, linatine, ergothioneine, creatinine, and cycloserine.

The lower alkyl-substituted amine which may have a substituent selected from the group consisting of hydroxy group and amino group includes an amine substituted with 1 to 3 straight or branched chain $C_{1-6}$ alkyl groups which may further have 1 to 3 substituents selected from the group consisting of hydroxy group and amino group, such as tris-(hydroxymethyl)aminomethane, ethylenediamine, diethanolamine, diisopropanolamine, triethanolamine, triisopropanol-amine, hydroxymethylamine, (2-hydroxyethyl) amine, 1-hydroxyethylamine, 3-hydroxypropylamine, 2,3-dihydroxy-ethylamine, 4-hydroxybutylamine, 3,4-dihydroxybutylamine, 1,1-dimethyl-2-hydroxyethylamine, 5-hydroxypentylamine, 6-hydroxyhexylamine, 2-methyl-3-hydroxypropylamine, 2,3,4-trihydrokybutylamine, aminomethylamine, 1-aminoethylamine, 3-aminopropylamine, 2,3-diaminoethylamine, 4-aminobutyl-amine, 3,4-diaminobutylamine, 1,1-dimethyl-2-aminoethylamine, 5-aminopentylamine, 6-aminohexylamine, 2-methyl-3-aminopropylamine, 2,3,4-triaminobutylamine, methylamine, ethylamine, propylamine, isopropylamine, butylamine, tert-butylamine, pentylamine, hexylamine, dimethylamine, diethylamine, dipropylamine, dibutylamine, dipentylamine, dihexylamine, N-methyl-N-ethylamine, N-ethyl-N-propylamine, N-methyl-N-butylamine, N-methyl-N-hexylamine, N-methyl-N-(2-hydroxyethyl)amine, N-methyl-N-(2-aminoethyl)amine, N-(2-aminoethyl)-N-(2-hydroxyethyl)amine and the like.

The amino sugar includes, for example, meglumine (i.e., N-methyl-D-glucamine), D-glucosamine, D-galactosamine, D-mannosamine, mycosamine, kanosamine, neosamine C, N-methyl-L-glucosamine, mycaminose, muramic acid, streptamine and the like.

Preferably, the amino acid is a basic amino acid such as L-arginine, L-lysine, and L-histidine; the lower alkyl-substituted amine which may have a substituent selected from the group consisting of hydroxy group and amino group is tris (hydroxymethyl)aminomethane, ethylenediamine, monoethanolamine, diethanolamine, diisopropanolamine, ethanolamine, triisopropanolamine and the like; and the amino sugar is meglumine, D-glucosamine and the like.

The amine salts of the carbostyril derivative can be prepared by reacting the derivative with an appropriate amine in a suitable solvent. The solvent used herein includes, for example, alcohols such as methanol, ethanol, and isopropanol; ketones such as acetone and methyl ethyl ketone; water; and the like; or the mixture thereof. The reaction is completed generally at room temperature to 150° C., preferably at room temperature to about 120° C., for several minutes to 7 days. The amount of the amine used is at least 0.1 mole, preferably 0.1 to 2 moles to 1 mole of the carbostyril derivative.

Into the reaction system, it may be optionally added an acid such as hydrochloric acid in order to prevent the dissociation of the carbostyril derivative.

Further, the amine salt of the carbostyril derivative may be formed in the course of preparing the aqueous preparation by adding an amine into an aqueous solution of the carbostyril derivative without the isolating as a salt.

The compounds of the present invention exhibit antiulcer activities, activities for increasing endogenic-prostaglandin E2, extinction or inhibition of active oxygen, inhibition of IL-8 production, inhibition of granulocyte activation, inhibition of expression of granulocyte adhesion factor, and the like, and are useful as an antiulcer drug, an agent for treating gastritis, a drug having efficacy derived from prostaglandin E2, such as an agent for preventing and treating ulcer, an antioxidant; an agent for preventing, protecting or treating an acute or chronic inflammatory disease. Additionally, they are useful for improving the biocompatibility of an artificial organ and an artificial blood vessel. Furthermore, the compounds of the invention are especially useful for preventing the relapse of peptic ulcer and inflammation.

The inflammatory diseases include, but not limited thereto, inflammatory dermatoses, such as inflammatory keratosis (psoriasis, etc.), atopic dermatitis, contact dermatitis and the like; autoimmune diseases which are chronic inflammatory diseases such as chronic rheumatoid, systemic lupus erthematosus (SLE), Behchet's disease and the like; inflammatory liver diseases such as hepatitis B, hepatitis C, alcoholic hepatitis; drug-induced allergic hepatitis and the like; inflammatory renal diseases such as nephritis, glomerulonephritis and the like; inflammatory respiratory diseases, such as bronchitis and the like; stomatitis; laryngitis; vocal cord inflammation; voice disorder; inflammation due to using an artificial organ and an artificial blood vessel; disorder of gastrointestinal tract mucosa and disorder of intestinal mucosa due to nonsteroidal antiinflammatory drug; and the like.

As to the disorder of intestinal mucosa, cryptogenic simple primary intestine ulcer, nonspecific colonic ulcer, ulcerative colitis due to nonspecific inflammation, Crohn's disease and the like are exemplified, and additionally disorders due to infection, cardiovascular disease, collagen disease, radiations, drugs and the like; etc. are also exemplified.

Additionally, the compounds of the invention have inhibitory effects of lowering somatostatin-release, antidiabetic effects, urease inhibiting effects and the like and are useful as a somatostatin-release inhibitor, an antidiabetic drug, and an urease inhibitor.

On the basis of the urease inhibiting effects, the compounds of the invention are useful for preventing and treating the diseases which may be caused by the enhancement of the urease activity by the increase of various bacteria and the production of ammonia, and thus the compounds may be used for preventing and treating disorders of gastric mucosa which may be caused by the production of ammonia by the increase of H. pylori. Additionally, the compounds may be used for improving and treating hyperammonemia and the diseases associated with hyperammonemia by depressing the production of ammonia in an intestinal tract, for example, they may be used for preventing and treating hepatic encephalopathies which are caused from liver diseases such as hepatitis, liver cirrhosis and the like; neuropsychiatric disorders; abnormality in electroencephalogram; and flapping tremor.

The compounds of the invention also have an increasing effect of goblet cell in eye, an increasing effect of mucus in eye, a facilitating effect of proliferation of corneal epithelial cell, and further an increasing effect of lacrimal fluid, and thus may be useful as a drug for treating dry eye, i.e., dry eye syndrome. Hence, the compounds of the invention may increase the production of mucin by increasing goblet cells in eye and prevent decreasing mucin as observed in dry eye while may hold the aqueous layer by way of increasing mucus in eye. The compounds also exhibit the action of increasing lacrimal fluid and thus are useful as a drug for treating dry eye. Further, the compounds of the invention are not only useful for Sjoegren's syndrome or Stevens-Johnson syndrome which may indicate dry eye syndrome, but also useful as a drug for preventing and/or treating various opthalmopathies which are indicated by the secondary disease of dry eye or by the reduction of goblet cells and the amount of mucus. Eyeballs affected by dry eye are so easy to be injured. Thus, the compounds of the invention are also useful as a drug for curing eye wound, especially corneal epithelium wound, or an intraocular perfusing and washing agents used in opthalmological operations (cataract, vitreous body, glaucoma), since the compounds have the effect for accelerating the proliferation of corneal epithelial cells.

The pharmaceutical composition of the compound of the present invention can be prepared into various forms of common pharmaceutical preparations by formulating the amine salt of carbostyril derivative as the active ingredient. The pharmaceutical formulations of the present invention are especially preferred to aqueous liquid formulations such as injections, ophthalmic solutions, oral solutions, enemas, gargles, ear drops, nasal drops, external liquid preparations and the like, and also including other conventional forms of pharmaceutical formulations, such as tablets, pills, powders, emulsions, granules, capsules, suppositories, aerosols, syrups and the like.

The aqueous solution preparation of the present invention can be prepared by adding the amine salt of carbostyril derivative into an aqueous solvent such as water, physiological saline and the like. The pharmaceutical formulations to be prepared in the form of a preparation when used, comprising the carbostyril derivative and the amine, can be prepared by adding an aqueous solvent when used, and thereby the amine salt of carbostyril derivative is formed in the preparation.

In preparing the pharmaceutical formulations of the present invention, conventional additives or excipients, such as a filler, an expander, a binder, a humectant, disintegrator, a surface activating agent, a lubricant, a flavor, a perfume, a sweetener, a coloring-agent, may be also used. Further, sustained release preparations can also be prepared by incorporating a suitable resin and the like. The formulations of the present invention for treating opthalmopathies are especially preferred to form a pharmaceutical preparation applicable for opthalmological purpose, such as an ophthalmic solution, an ophthalmic ointment and the like, depending on the symptoms to be applied.

In case of preparing the injections of the present invention, they are prepared in the form of a solution, an emulsion or a suspension, and generally they are sterilized and preferably made isotonic to the blood. For the purpose of forming into a solution, an emulsion or a suspension, any diluents which are widely used in this field can be applied, for example, solvents such as water, ethyl alcohol, propylene glycol and the like; stearyl alcohols such as ethoxylated isostearyl alcohol, polyoxylated isostearyl alcohol and the like; emulsifying agents such as fatty acid esters of polyoxyethylene sorbitan and the like; suspending agents such as arabic gum, sodium carboxymethyl cellulose, hydroxypropylmethyl cellulose and the like. In the case of preparing an injection solution isotonic to the blood, a sufficient amount of sodium chloride, glucose, D-mannitol or the like may be contained therein. Additionally, conventional dissolving adjuvants such as Polysorbate 80 and the like; buffering agents such as citric acid, sodium citrate, phosphoric acid, lactic acid and the like; soothing agents such as glycerin and the like; and so on may be also be contained therein. Further, when necessary, coloring agents, preservatives, flavors, perfumes, sweeteners and the like, other medicines may be contained therein.

The pharmaceutical preparations applicable for opthalmological purpose, such as ophthalmic solutions, ophthalmic ointments and the like, are prepared in accordance with a conventional method by using usual vehicles (diluting agents) acceptable for opthalmological purpose. Thus, they are prepared by mixing the active ingredient with suitable base material(s), then the mixture is subjected to sterilizing treatment. For example, in case of preparing ophthalmic ointments, conventional emulsion type ointment base, water-soluble type ointment base, suspension type ointment base and the like can be employed. As to typical examples of these base materials, white petrolatum, refined lanolin, liquid paraffin and the like can be exemplified. In case of producing ophthalmic solutions, sterilized distilled water can be employed as typical diluting agent. Further, if necessary, a dissolving additive, a buffering agent, an antioxidant; an antiseptic agent, an isotonic agent, a pH-controlling agent and the like can be formulated with a pharmaceutical preparation applicable for opthalmological purpose. As to the dissolving additives, sodium carboxymethyl cellulose; polyoxyethyleneglycol ethers, such as polyoxyethylene lauryl ether, polyoxyethylene oleyl ether and the like; polyethylene glycol higher fatty acid esters, such as polyethylene glycol monolaurate, polyethylene glycol monooleate and the like; polyoxyethylene sorbitan mono-laurate; polyoxyethylene fatty acid esters and the like can be exemplified. As to the buffering agent, sodium phosphate, sodium hydrogen phosphate, potassium hydrogen phosphate, boric acid, sodium borate, citric acid, sodium citrate, tartaric acid, sodium tartrate, acetic acid, sodium acetate, ε-aminocaproic acid, sodium glutamate and the like can be exemplified. As to the antioxidant, sodium sulfite, sodium pyrosulfite, sodium hydrogen sulfite, sodium thiosulfite, ascorbic acid and the like can be exemplified. As to the antiseptic agent, chlorobutanol, benzalkonium chloride, benzethonium chloride, phenylmercury salt, thimerosal, phenethyl alcohol, methylparaben, propylparaben and the like can be exemplified. As to isotonic agent, sodium chloride, glucose, D-mannitol, glycerin and the like can be exemplified. As to the pH-controlling agent, sodium hydroxide, hydrochloric acid and the like can be exemplified.

For the purpose of preparing tablets, any known ingredients which are used widely in this field can be applied, for example, excipients such as lactose, white sugar, sodium chloride, glucose, urea, starch, calcium carbonate, kaolin, crystalline cellulose, silicic acid and the like; binders such as water, ethanol, propanol, simple syrup, glucose solution, starch solution, gelatin solution, carboxymethyl cellulose, shellac, methyl cellulose, potassium phosphate, polyvinyl pyrrolidone and the like; disintegrators such as dry starch, sodium alginate, agar powder, laminaran powder, sodium hydrogen carbonate, calcium carbonate, polyoxyethylene sorbitan fatty acid esters, sodium lauryl sulfate, monoglycerides of stearic acid, starch, lactose and the like; disintegration inhibitors such as white sugar, stearin, cacao butter, hydrogenated oil and the like; absorption accelerators such as quaternary ammonium base, sodium lauryl sulfate and the like; humectants such as glycerin, starch and the like; adsorbents such as starch, lactose, kaolin, bentonite, colloidal silicic acid and the like; lubricants such as refined talc, stearic acid salts, boric acid powder, polyethylene glycols and the like. Further, when necessary, the tablets can be prepared in the form of common coated tablets, for example, sugar-coated tablets, gelatin film-coated tablets, enteric film-coated tablets, film-coated tablets, or in the form of double-layers tablets and multiple-layers tablets.

For the purpose of preparing pills, any known ingredients which are widely used in this field can be applied, for example, excipients such as glucose, lactose, starch, cacao butter, hydrogenated vegetable oils kaolin, talc and the like; binders such as arabic gum powder, tragacanth gum powder, gelatin, ethanol and the like; and disintegrators such as laminaran, agar and the like can be exemplified. For the purpose of preparing suppositories, any known ingredients which are widely used in this field can be applied, for example, polyethylene glycols, cacao butter, higher alcohols, esters of higher alcohol, gelatin, semi-synthesized glycerides and the like can be exemplified.

The aerosols are usually prepared in the form of a sterilized liquid or suspension, and therein propellants are added. For the purpose of preparing the liquids and suspensions, any diluents which are used widely in this field can be applied, for example, above-mentioned diluents for the injections can be exemplified. Any propellants which are used widely in this field can be applied, for example, chlorofluorocarbons such as flon 12 and the like; liquefied gas-propellants such as flon 123 and the like; and compressed gas-propellants such as nitrogen, carbon dioxide and the like can be exemplified. The aerosols may include conventional dissolving adjuvants, buffering agents and the like, further when necessary, coloring agents, preservatives, flavors, perfumes, sweeteners and the like.

The amount of the amine salt of the carbostyril derivative of the present invention to be contained in the formulation is not specifically restricted and it can suitably be selected from a wide range, and generally 1 to 70%, preferably 5 to 50% by weight of the whole composition. For especially preferably pharmaceutical preparations applicable for opthalmological purpose, the amount is generally 0.005 to 5%, preferably 0.01 to 3% by weight of the whole composition. Method for the administration is not specifically restricted. Thus, the pharmaceutical preparation may be administered by acceptable methods, depending upon the form of each preparation, the age of patient, the distinction of sex and other conditions, as well as the severity of diseases of the patient. For example, tablets, pills, a liquid preparation, a suspension preparation, an emulsion preparation, a granular preparation, a syrup preparation and capsules are orally administered. An injection preparation is intravenously administered alone or in combination with a conventional auxiliary solution such as a glucose solution, an amino acid solution and the like. Additionally, when necessary, the injection preparation is administered alone intramuscularly, intradermally, subcutaneously or intraperitoneally. Suppositories are endorectally administered. The present pharmaceutical preparations applicable for opthalmological purpose may be administered by a method similar to those of conventional preparations, for example, ophthalmic ointments are administered on eyes. Ophthalmic solutions are administered by a method similar to those of conventional preparations, for example, 1 to 2 drops of an ophthalmic solution is dropped in eyes from a suitable eye drop container, or an ophthalmic solution may be administered in eyes by use of a spraying device.

Dosage of the agent of the present invention may be suitably selected depending upon the method for administration, the age of patient, the distinction of sex, and other conditions, as well as the severity of diseases of the patient, and generally the agent of the invention may preferably contain 0.6 to 50 mg/kg of body weight/day of the carbostyril derivative (1). Further 10 to 1000 mg of the active ingredient may be contained in the administrative unit form. The pharmaceutical preparations applicable for opthalmological purpose, such as an ophthalmic solution or an ophthalmic ointment, are administered within a range of 1 to 15 times, preferably 1 to 10 times a day.

The amine salts of carbostyril derivative of the present invention have a superior water solubility, and are useful for the preparation in the form of a solution such as injections, ophthalmic solutions, oral solutions, enemas, gargles, ear drops, nasal drops, external liquid preparations and the like. Especially, they have some advantages such as being easy to keep the uniformity of content; not necessary to control the particle distribution; not necessary to add the suspending agent, dispersing agent and the like; easy to carry out the terminal sterilization by steam or the sterilization by filtration; etc. and thus the desired pharmaceutical products can be prepared industrially, simply and easily. Especially, the ophthalmic solutions of the invention have some advantages, for example, not to need the complicated re-dispersion like a suspension preparation, and good feelings in use such as good looks.

BEST MODE FOR CARRYING OUT THE INVENTION

The present invention will be explained more specifically by the way of the following examples, examples of pharmaceutical preparation and pharmacologic experiments.

Example 1

2-(4-chlorobenzoylamino)-3-(2-quinolon-4-yl)propionic acid.L-arginine salt

A suspension of 3.88 g of 2-(4-chlorobenzoylamino)-3-(2-quinolon-4-yl)propionic acid (10.5 mmol) and 2.00 g L-arginine (11.5 mmol) in 200 mL of ethanol was refluxed for 30 minutes. To the mixture was added 20 mL of water, and the reflux was continued, then the reaction product was temporarily completely dissolved. After that, precipitates appeared under the reflux. After stopped the heating, the reaction mixture was cooled to room temperature, and further cooled in ice-water. The precipitates were taken by filtration through a Nutsche funnel, washed with ethanol on the Nutsche funnel, and dried with a blower at 50° C. for 20 hours to give 5.38 g of 2-(4-chlorobenzoylamino)-3-(2-quinolon-4-yl)propionic acid.L-arginine salt (95% yield) as a white crystal.

$^1$H NMR (DMSO-d6) δ=1.43-1.92 (4H, m), 2.95-3.65 (5H, m), 4.41-4.58 (1H, m), 6.42 (1H, s), 7.20 (1H, dd, J=8.1, 7.6 Hz), 7.30 (1H, d, J=8.2 Hz), 7.47 (1H, dd, J=8.2, 7.6 Hz), 7.49 (2H, d, J=8.4 Hz), 7.81 (2H, d, J=8.4 Hz), 7.96 (1H, d, J=8.1 Hz), 8.34 ppm 1H, d, J=8.2 Hz).

Example 2

2-(4-chlorobenzoylamino)-3-(2-quinolon-4-yl)propionic acid.L-lysine salt

A suspension of 1.94 g of 2-(4-chlorobenzoylamino)-3-(2-quinolon-4-yl)propionic acid (5.23 mmol) and 0.84 g of L-lysine (5.76 mmol) in ethanol (100 mL) was refluxed for 30 minutes. To the mixture was added 25 mL of water, and the reflux was continued, then the reaction product was completely dissolved. After that, precipitates appeared under the reflux. After stopped the heating, the reaction mixture was cooled to room temperature and further cooled in ice-water. The precipitates were taken by filtration through a Nutsche funnel, washed with ethanol on the Nutsche funnel, and dried with a blower at 60° C. over night to give 1.46 g of 2-(4-chlorobenzoylamino)-3-(2-quinolon-4-yl)propionic acid.L-lysine salt as a white crystal (54% yield).

$^1$H NMR (DMSO-d6) δ=1.18-1.80 (6H, m), 2.74 (2H, br.d, J=6.7 Hz), 3.08 (1H, br.dd, J=13.6, 9.8 Hz), 3.29 (1H, br.t, J=5.8 Hz), 3.43-3.59 (1H, m), 4.48 (1H, br.ddd, J=9.8, 8.0, 3.6 Hz), 6.44 (1H, s), 7.18 (1H, dd, J=8.1, 7.5 Hz), 7.31 (1H, d, J=7.9 Hz), 7.45 (1H, dd, J=7.9, 7.5 Hz), 7.48 (2H, d, J=8.5 Hz), 7.81 (2H, d, J=8.5 Hz), 7.96 (1H, d, J=8.1 Hz), 8.40 ppm (1H, d, J=8.0 Hz)

Example 3

2-(4-chlorobenzoylamino)-3-(2-quinolon-4-yl)propionic acid-.½ ethylenediamine salt (A): A suspension of 2.00 g of 2-(4-chlorobenzoylamino)-3-(2-quinolon-4-yl)propionic acid (5.39 mmol) and 0.18 mL of ethylenediamine (2.69 mmol) in 100 mL of ethanol was refluxed for 30 minutes. Water was added thereto by each 5 mL portion until the reaction product was dissolved. The reaction product was completely dissolved when 35 mL of water in total was added. After the heating was stopped, the mixture was cooled to room temperature, and then the crystals were precipitated. After the reaction mixture was further cooled in ice-water, the precipitated crystals were taken by filtration through a Nutsche funnel, and dried with a blower at 60° C. to give 1.92 g 2-(4-chlorobenzoylamino)-3-(2-quinolon-4-yl)propionic acid.½ ethylenediamine salt (89% yield) as a white crystal.

(B): A suspension of 2.00 g of 2-(4-chlorobenzoylamino)-3-(2-quinolon-4-yl)propionic acid (5.39 mmol), 0.40 mL of ethylenediamine (5.98 mmol) in 100 mL of ethanol was refluxed for 30 minutes. Water was added thereto by each 5 mL portion until the reaction product was dissolved. The reaction product was completely dissolved when 25 mL of water in total was added. Then, the heating was stopped and the mixture was cooled to room temperature, but any crystals were not precipitated. So the solvent was removed off under a reduced pressure. To the residue was added 50 mL of ethanol, dispersed under a reflux for the purification and cooled to room temperature. The resulting crystals were taken by filtration through a Nutsche funnel, and dried with a blower at 60° C. to give 1.96 g of 2-(4-chlorobenzoylamino)-3-(2-quinolon-4-yl)propionic acid.½ ethylenediamine salt (91% yield) as a white crystal.

$^1$H NMR (DMSO-d6) δ=2.87 (2H, s), 3.11 (1H, br.dd, J=13.9, 9.8 Hz), 3.52 (1H, br.dd, J=13.9, 3.5 Hz), 4.50-4.57 (1H, m), 6.41 (1H, s), 7.20 (1H, dd, J=8.0, 7.6 Hz), 7.30 (1H, d, J=7.5 Hz), 7.48 (1H, dd, J=8.0, 7.5 Hz), 7.52 (2H, d, J=8.5 Hz), 7.80 (2H, d, J=8.5 Hz), 7.93 (1H, d, J=7.6 Hz), 8.40 ppm (1H, d, J=8.0 Hz).

Example 4

2-(4-chlorobenzoylamino)-3-(2-quinolon-4-yl)propionic acid-.tris(hydroxymethyl)aminomethane salt A suspension of 2.00 g of 2-(4-chlorobenzoylamino)-3-(2-quinolon-4-yl)propionic acid (5.39 mmol) and 0.72 g of tris (hydroxymethyl)aminomethane (5.94 mmol) in 100 mL of ethanol was refluxed for 30 minutes. Water was added thereto by each 5-10 mL portion until the reaction product was dissolved. The reaction product was completely dissolved when 40 mL of water in total was added. Then, the heating was stopped and the mixture was cooled to room temperature and further cooled with ice-water, but any crystals were not precipitated. And then the solvent was removed off under a reduced pressure. To the residue was added ethanol and the mixture was concentrated under a reduced pressure. To the residue was added 50 mL of ethanol, and the mixture was stirred at room temperature. The resulting precipitates were separated by filtration through a Nutsche funnel, and dried with a blower at 60° C. to give 2.58 g of 2-(4-chlorobenzoylamino)-3-quinolon-4-yl)propionic acid tris(hydroxymethyl)aminomethane salt (97% yield) as a white crystal.

$^1$H NMR (DMSO-d6) δ=3.07 (1H, br.dd, J=13.8, 10.1 Hz), 3.47 (6H, s), 3.54 (1H, br.dd, J=13.9, 3.3 Hz), 4.49-4.56 (1H, m), 6.41 (1H, s), 7.21 (1H, dd, J=8.1, 7.7 Hz), 7.31 (1H, d, J=7.5 Hz), 7.45 (1H, dd, J=8.1, 7.5 Hz), 7.51 (2H, d, J=8.5 Hz), 7.81 (2H, d, J=8.5 Hz), 7.94 (1H, d, J=7.7 Hz), 8.38 ppm (1H, d, J=6.3 Hz).

Example 5

2-(4-chlorobenzoylamino)-3-(2-quinolon-4-yl)propionic acid.diethanolamine salt

A suspension of 2.00 g of 2-(4-chlorobenzoylamino)-3-(2-quinolon-4-yl)propionic acid (5.39 mmol) and 0.62 g of diethanolamine (5.90 mmol) in 100 mL of ethanol was refluxed for 30 minutes. The reaction product was completely dissolved without adding water. Then, the heating was stopped and the mixture was cooled to room temperature and further cooled with ice-water. The resulting precipitates were separated by filtration through a Nutsche funnel, and dried with a blower at 60° C. to give 1.95 g of 2-(4-chlorobenzoylamino)-3-(2-quinolon-4-yl)-propionic acid.diethanolamine salt (76% yield) as a white crystal.

$^1$H NMR (DMSO-d6) δ=2.89 (4H, t, J=5.4 Hz), 3.10 (1H, br.dd, J=13.9, 9.9 Hz); 3.52 (1H, br.dd, J=3.6 Hz), 3.61 (4H, t, J=5.4 Hz), 4.50-4.56 (1H, m), 6.41 (1H, s), 7.21 (1H, dd, J=8.1, 7.6 Hz), 7.31 (1H, d, J=7.5 Hz), 7.48 (1H, dd, J=8.1, 7.5 Hz), 7.52 (2H, d, J=8.5 Hz), 7.81 (2H, d, J=8.5 Hz), 7.94 (1H, d, J=7.6 Hz), 8.44 ppm (1H, d, J=8.2 Hz).

Example 6

2-(4-chlorobenzoylamino)-3-(2-quinolon-4-yl)propionic acid.diisopropanolamine salt A suspension of 2.00 g of 2-(4-chlorobenzoylamino)-3-(2-quinolon-4-yl)propionic acid (5.39 mmol) and 0.79 g of diisopropanolamine (5.93 mmol) in 100 mL of ethanol was refluxed for 30 minutes. The reaction product was completely dissolved without adding water. Then, the heating was stopped and the mixture was cooled to room temperature and further cooled with ice-water. The resulting precipitates were separated by filtration through a Nutsche funnel, and dried with a blower at 60° C. to give 1.66 g of 2-(4-chlorobenzoylamino)-3-(2-quinolon-4-yl)-propionic acid.diisopropanolamine salt (61% yield) as a white crystal.

$^1$H NMR (DMSO-d6) δ=1.07 (3H, d, J=6.2 Hz), 1.13 (3H, d, J=6.2 Hz), 2.54-2.68 (2H, m), 2.77 (2H, dd, J=12.2, 3.5 Hz), 3.08-3.18 (1H, m), 3.43-3.56 (1H, m), 3.75-3.92 (2H, m), 4.47-4.60 (1H, m), 6.41 (1H, s), 7.21 (1H, dd, J=8.0, 7.7 Hz), 7.30 (1H, d, J=7.5 Hz), 7.49 (1H, t, J=7.5 Hz), 7.52 (2H, d, J=8.6 Hz), 7.81 (2H, d, J=8.6 Hz), 7.93 (1H, d, J=7.7 Hz), 8.48 ppm (1H, d, J=8.1 Hz).

Example 7

2-(4-chlorobenzoylamino)-3-(2-quinolon-4-yl)propionic acid-.meglumine salt

To 3.7 g of 2-(4-chlorobenzoylamino)-3-(2-quinolon-4-yl) propionic acid (10 mmol) was added 1 main aqueous solution of meglumine (10 ml, 10 mmol), and heated at 50° C. to be dissolved. To the solution was added an aqueous solution of equimolar mixture of meglumine and hydrochloric acid (0.5 mol/L; 20 mL), and the mixture was cooled. The resulting precipitates were separated by filtration, washed with water, and dried under a reduced pressure at room temperature to give 0.9 g of 2-(4-chlorobenzoylamino)-3-(2-quinolon-4-yl) propionic acid.meglumine salt (16% yield) as a white crystal.

$^1$H NMR (DMSO-d6) δ=2.82-3.14 (3H, m), 3.37-3.73 (6H, m), 3.82-3.94 (1H, m), 4.52 (1H, ddd, J=9.6, 6.2, 3.5 Hz), 6.41 (1H, s), 7.20 (1H, dd, J=8.0, 7.2 Hz), 7.30 (1H, d, J=7.8 Hz), 7.48 (1H, dd, J=7.8, 7.2 Hz), 7.51 (2H, d, J=8.5 Hz), 7.80 (2H, d, J=8.5 Hz), 7.94 (1H, d, J=8.0 Hz), 8.37 ppm (1H, d, J=8.2 Hz).

Example 8

Water-Solubility Test at 25° C.

Compound A: 2-(4-chlorobenzoylamino)-3-(2-quinolon-4-yl)-propionic acid

Preparation of the Test Solution 0.5 g of the salt obtained in the above Examples 1-7 was transferred into a 50 mL centrifugal tube, and 5 mL of water was added thereto, and the mixture was shaken by a shaker for 3 hours (5 days for meglumine salt) in a thermostat (25° C.). After shaking, the mixture was filtered through a 0.45 μm membrane filter (0.2 μm for meglumine salt). 1 mL of the filtrate was precisely pipetted and thereto was added 50% DMF so as to be totally 50 mL in precise. 2 mL of this solution was precisely pipetted and thereto was added 50% DMF so as to be totally 20 mL in precise to give a sample solution.

Preparation of the Standard Solution 0.01 g of Compound A was dissolved in 5 mL of dimethylformamide (DMF) and thereto was added 50% DMF so as to be totally 100 mL precisely to give the standard solution (1). 5 mL of the standard solution (1) was precisely pipetted and thereto was added 50% DMF so as to be totally 10 mL in precise to give the standard solution (2). 1 ml of the standard solution (1) was precisely pipetted and thereto was added 50% DMF so as to be totally 10 mL in precise to give the standard solution (3). 1 mL of the standard solution (3) was precisely pipetted and thereto was added 50% DMF so as to be totally 10 mL in precise to give the standard solution (4).

Chromatography

Using each 10 μL of the sample solutions and the standard solutions, the liquid chromatographic analyses were carried out in the following conditions. A calibration curve was drawn based on the peak areas of Compound A and the concentrations of Compound A obtained from the standard solutions (1)-(4). Using this calibration curve, the concentration of Compound A in the sample solution was calculated from the peak area of compound A of the sample solution and the data were corrected by means of dilution ratio, and thereby the solubilities (%) of various salts were determined.

| Test Conditions | |
|---|---|
| Detector | UV Spectrophotometer (Wave Length: 254 nm) |
| Column | Cosmosil 5C$_{18}$ (4.6 mm I.D. × 15 cm) |
| Column Temperature | A constant temperature of around 25° C. |
| Mobile Phase | 0.58 g of anhydrous sodium monohydrogen phosphate and 2.0 g of potassium dihydrogen phospate were dissolved in 1000 mL of water. To 830 mL of the solution was added 170 mL of acetonitrile. |
| Flow Rate | 1.0 mL/min |

| Compounds | Solubility (%) |
|---|---|
| Compound A•L-arginine salt | 1.0% |
| Compound A•L-lysine salt | 2.2% |
| Compound A•1/2 ethylenediamine salt | 0.05% |
| Compound A•diethanolamine salt | 4.1% |
| Compound A•diisopropanolamine salt | 2.9% |
| Compound A•tris (hydroxymethyl) aminomethane salt | 0.2% |
| Compound A•meglumine salt | 8.6% |
| Compound A | 0.0006% |

Example 9

Solubility Test at 25° C. of the Salt in a Preparation Prepared When Used Without Isolating the Salt To Compound A was added an equimolar amount of each amine compound and then added water in such an amount that the salt would not be completely dissolved, and shaken by a shaker for 7 days in a thermostat (25° C.). And then as to a sample to which arginine was added, the suspension was filtered through a 0.2 μm membrane filter. As to samples to which lysine, diisopropanolamine, meglumine, monoethanolamine or diethanolamine was added, the mixture could not be filtered due to the solidification, and hence, water was further added to the mixture until it became to be possible to be filtered. And then the mixture was filtrated through a 0.2 μm membrane filter. According to the same method as Example 8, the solubilities (%) of each salt was measured by HPLC.

| Compound | Solubility (%) |
|---|---|
| Compound A•L-arginine salt | 0.78% |
| Compound A•L-lysine salt | >3.2% |
| Compound A•diisopropanolamine salt | >7.4% |
| Compound A•meglumine salt | >12% |

-continued

| Compound | Solubility (%) |
|---|---|
| Compound A•monoethanolamine salt | >3.3% |
| Compound A•diethanolamine salt | >7.4% |

Example of Pharmaceutical Preparation 1

| | |
|---|---|
| 2-(4-Chlorobezoylamino)-3-(2-quinolon-4-yl)-propionic acid•diethanolamine salt | 0.2 g |
| Benzalkonium chloride | 0.01 g |
| Sodium dihydrogen phosphate | 0.56 g |
| Potassium dihydrogen phosphate | 0.8 g |
| Distilled water | q.s. |
| Total | 100.0 mL |

Above ingredients were dissolved in distilled water and sterilized with a suitable filter to prepare the formulation of the present invention in the form an ophthalmic solution.

Example of Pharmaceutical Preparation 2

| | |
|---|---|
| 2-(4-Chlorobenzoylamino)-3-(2-quinolon-4-yl)-propionic acid•L-arginine salt | 150 g |
| Avicel (Trademark, Asahi KASEI) | 40 g |
| Corn starch | 30 g |
| Magnesium stearate | 2 g |
| Hydroxypropylmethyl cellulose | 10 g |
| Polyethylene glycol-6000 | 3 g |
| Castor oil | 40 g |
| Methanol | 40 g |

The compound of the invention, Avicel, corn starch and magnesium stearate were mixed and milled, and then compressed with punches (10 mm R for sugar-coat). The resulting tablets were coated with a film coating agent comprising hydroxypropylmethyl cellulose, polyethylene glycol-6000, castor oil and methanol to prepare the film coating tablets.

Example of Pharmaceutical Preparation 3

| | |
|---|---|
| 2-(4-Chlorobenzoylamino)-3-(2-quinolon-4-yl)propionic acid•diisopropanolamine salt | 150 g |
| Citric acid | 1.0 g |
| Lactose | 33.5 g |
| Dicalcium phosphate | 70.0 g |
| Pluronic F-68 | 30.0 g |
| Sodium lauryl sulfate | 15.0 g |
| Polyvinyl pyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium lauryl sulfate | 3.0 g |
| Dry magnesium stearate | 3.0 g |
| ethanol | q.s. |

The compound of the present invention, citric acid, lactose, dicalcium phosphate, Pluronic F-68 and sodium lauryl sulfate are mixed. The above mixture is screened through a No. 60 screen and wet-granulated with alcoholic solution comprising polyvinylpyrrolidone, Carbowax 1500 and 6000. When necessary, some alcohol is added to make the powder to paste-like solid. Corn starch is added thereto, the mixing is continued to form uniform particles. The granules are sieved through No. 10 screen, put on tray and dried at 100° C. for 12-14 hours in an oven. The dried granules are sieved through. No. 16 screen, to the sieved granules are added dry sodium lauryl sulfate and dry magnesium stearate, then the whole ingredients are mixed and compressed into the shape of desired form by using a tabletting machine. The core portions are treated with a varnish, the surfaces thereof are sprayed with talc for preventing the surfaces from the absorption of moisture. The surface of the core portions are further coated with a primary coating layer. The surface are further coated with a varnish to make a sufficient number of layers for preparing coated tablets for oral administration. In order to make the coated tablets into complete spherical form and to make the surfaces smooth, the coated tablets are further coated with primary coating layers and smoothing coating layers. The coated tablets are color-coated until the desired color of the surface is obtained. After dried, the coated tablets are polished to make them uniform gloss.

Example of Pharmaceutical Preparation 4

| | |
|---|---|
| 2-(4-Chlorobenzoylamino)-3-(2-quinolon-4-yl)propionic acid•L-lysine salt | 2 g |
| Lactic acid | 0.01 g |
| Sodium lactate | 0.1 g |
| D-Mannitol | 3.5 g |
| Distilled water | q.s. |
| Total | 100 mL |

The above-mentioned compound of the invention and the additives are dissolved in distilled water, transferred into glass vials and then sterilized by steam to prepare the injectable solution.

Example of Pharmaceutical Preparation 5

| | |
|---|---|
| 2-(4-chlorobenzoylamino)-3-(2-quinolon-4-yl)propionic acid•meglumine salt | 2 g |
| Citric acid | 1.0 g |
| Sodium citrate | 0.3 g |
| Sucrose | 15 g |
| Methylparaben | 0.2 g |
| Propylparaben | 0.02 g |
| ethanol | 5 mL |
| Orange flavor | 0.1 g |
| Red No. 3 | q.s. |
| Distilled water | q.s. |
| Total | 100 mL |

The above-mentioned compound of the invention and the additives are formulated to prepare the oral solution.

INDUSTRIAL APPLICABILITY

The amine salts of carbostyril derivative of the present invention have superior water solubility, and are especially useful for the preparation of formulations in the form of an aqueous solution, such as injections, ophthalmic solutions, oral solutions and the like; additionally keep the superior pharmacological effectiveness of the carbostyril derivatives, such as antiulcer activity, activities for increasing endogenic-prostaglandin E2, extinction or inhibition of active oxygen, inhibition of IL-8 production, inhibition of granulocyte activation, inhibition of expression of granulocyte adhesion factor, inhibitory activity of lowering somatostatin-release, antidiabetic activity, urease inhibitory activity, and further an increasing of goblet cell in eye, an increasing of mucus in eye, an increasing of lacrimal fluid; and are useful as drugs for treating various diseases, especially as ophthalmic drops for treating various ophthalmopathy such as dry eye.

The invention claimed is:

1. An amine salt of a carbostyril derivative comprising 2-(4-chlorobenzoylamino)-3-(2-quinolon-4-yl)propionic acid, and an amine selected from the group of an amino acid; a $C_{1-6}$ alkyl-substituted amine which may have a substituent selected from the group consisting of hydroxy group and amino group; and an amino sugar.

2. A pharmaceutical formulation comprising the amine salt of the carbostyril derivative according to claim 1 as the active ingredient.

3. A pharmaceutical formulation which is prepared in the form of an aqueous solution by adding an aqueous solvent when used, comprising 2-(4-chlorobenzoylamino)-3-(2-quinolon-4-yl)propionic acid, and
an amine selected from the group of an amino acid; a $C_{1-6}$ alkyl-substituted amine which may have a substituent selected from the group consisting of hydroxy group and amino group; and an amino sugar.

* * * * *